United States Patent

Rolland et al.

[11] Patent Number: 5,993,427
[45] Date of Patent: Nov. 30, 1999

[54] EVERTING TUBE STRUCTURE

[75] Inventors: Richard Andrew Rolland, Toronto; Richard Grodecki, Trenton; Raymond Laborie, St. Bruno, all of Canada

[73] Assignee: Laborie Medical Technologies Corp., Williston, Vt.

[21] Appl. No.: 08/907,098

[22] Filed: Aug. 6, 1997

Related U.S. Application Data

[60] Provisional application No. 60/032,295, Dec. 3, 1996.

[51] Int. Cl.[6] .................................................. A61M 9/00
[52] U.S. Cl. .......................................................... 604/271
[58] Field of Search .................................. 604/264, 271, 604/280

[56] References Cited

U.S. PATENT DOCUMENTS

| | | |
|---|---|---|
| 3,050,060 | 8/1962 | Hoffman . |
| 3,168,092 | 2/1965 | Silverman . |
| 3,433,214 | 3/1969 | Silverman . |
| 3,502,069 | 3/1970 | Silverman . |
| 3,506,011 | 4/1970 | Silverman . |
| 3,589,356 | 6/1971 | Silverman . |
| 3,908,635 | 9/1975 | Viek . |
| 3,911,927 | 10/1975 | Rich et al. ............................. 604/271 |
| 4,043,345 | 8/1977 | Kramann et al. ...................... 604/271 |
| 4,077,610 | 3/1978 | Masuda . |
| 4,109,659 | 8/1978 | Sheridan . |
| 4,329,995 | 5/1982 | Anthracite ........................... 604/540 X |
| 4,493,711 | 1/1985 | Chin et al. ............................. 606/192 |
| 4,530,698 | 7/1985 | Goldstein et al. . |
| 4,604,094 | 8/1986 | Shook . |
| 4,606,347 | 8/1986 | Fogarty et al. . |
| 4,990,138 | 2/1991 | Bacich et al. ........................ 604/271 X |
| 5,045,070 | 9/1991 | Grodecki et al. . |
| 5,236,423 | 8/1993 | Mix et al. ............................... 604/271 |

*Primary Examiner*—Wynn Wood Coggins
*Assistant Examiner*—A. T. Nguyen
*Attorney, Agent, or Firm*—Sherman & Shalloway

[57] ABSTRACT

An everting tube structure comprises: a flexible collapsible tube having a first open end and a second open end, the flexible collapsible tube having a first portion proximate the first open end and a second portion, the first portion having a first part adjacent the first open end and a second part adjacent the second portion, the second portion having been folded at an angle to the first portion and wound around the second part of the first portion to form a hollow cylinder; and a tube member having an open end, the first open end of the tube being fluid-tightly, circumferentially attached to the open end of the tube member. Thus, the present invention provides an everting tube structure of simple construction, which can be easily produced, which allows easy and/or self-administration, and which has an enhanced self-guiding ability.

14 Claims, 8 Drawing Sheets

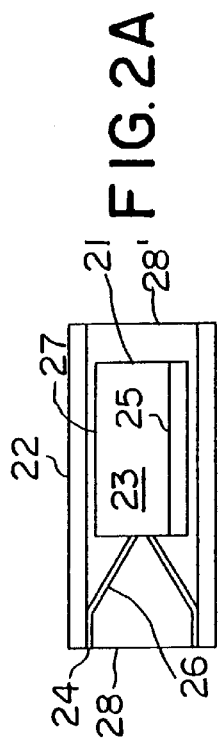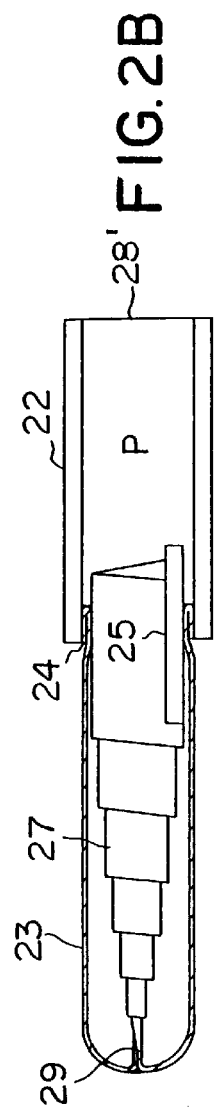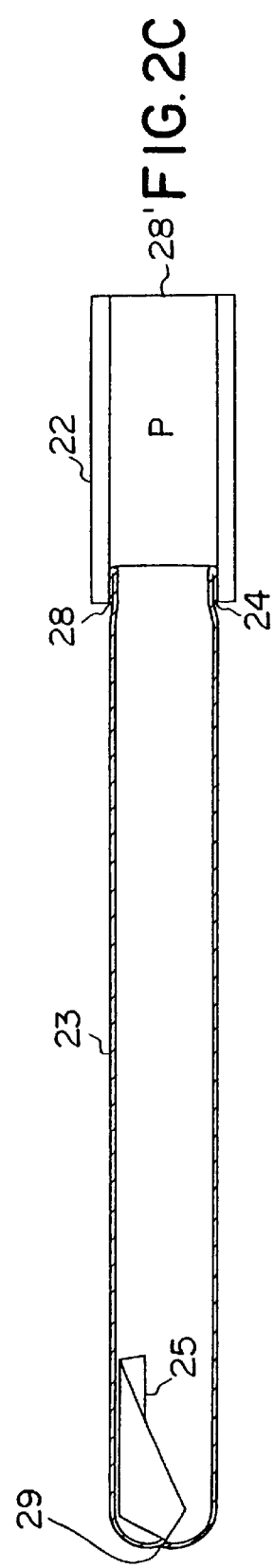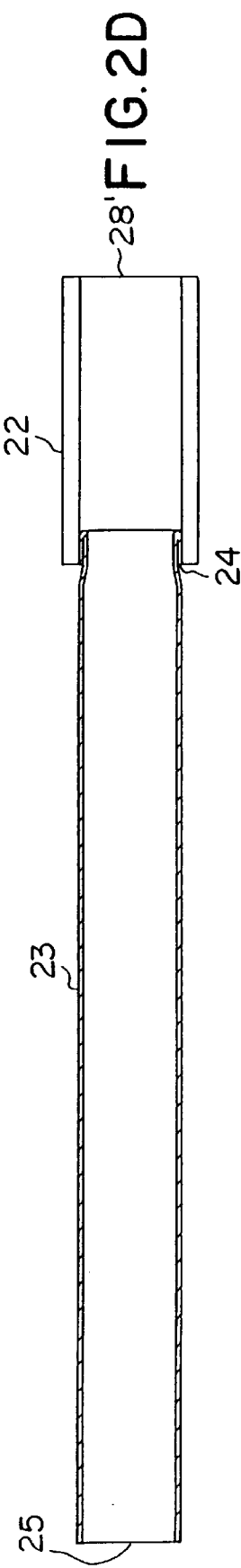

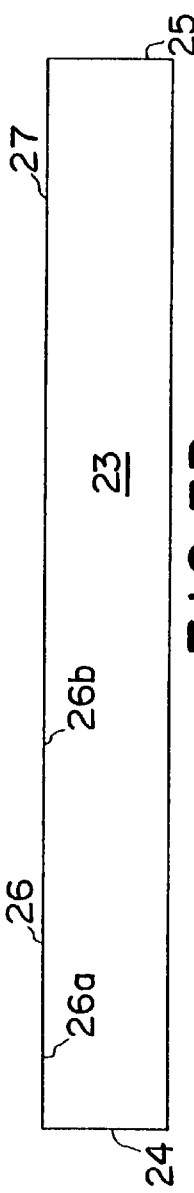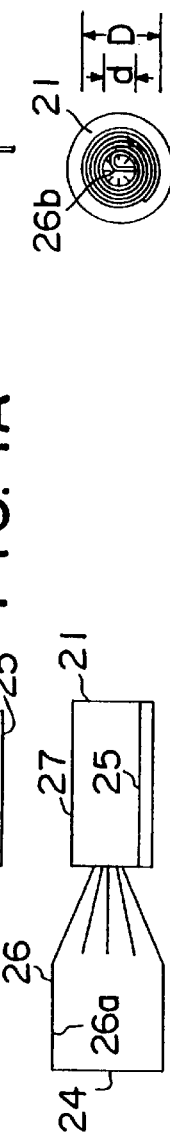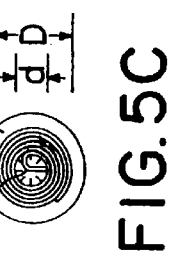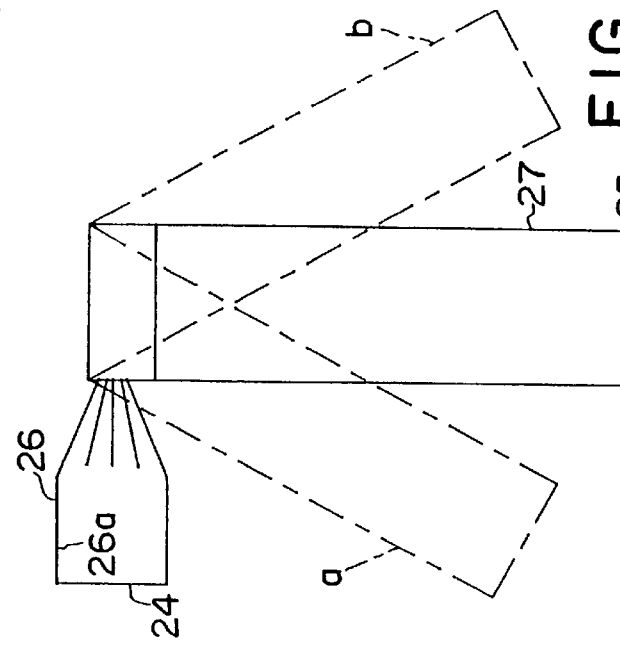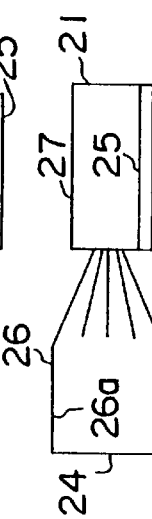

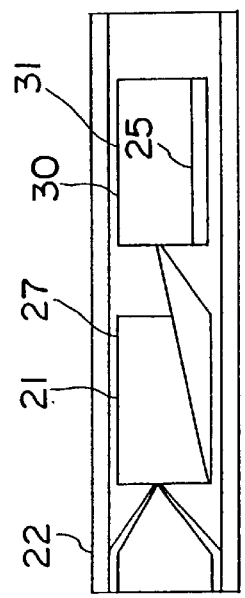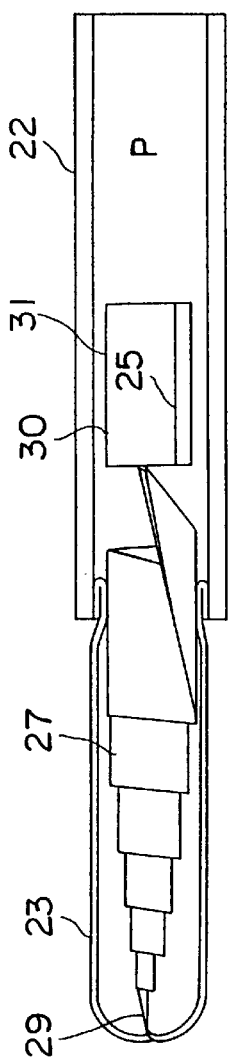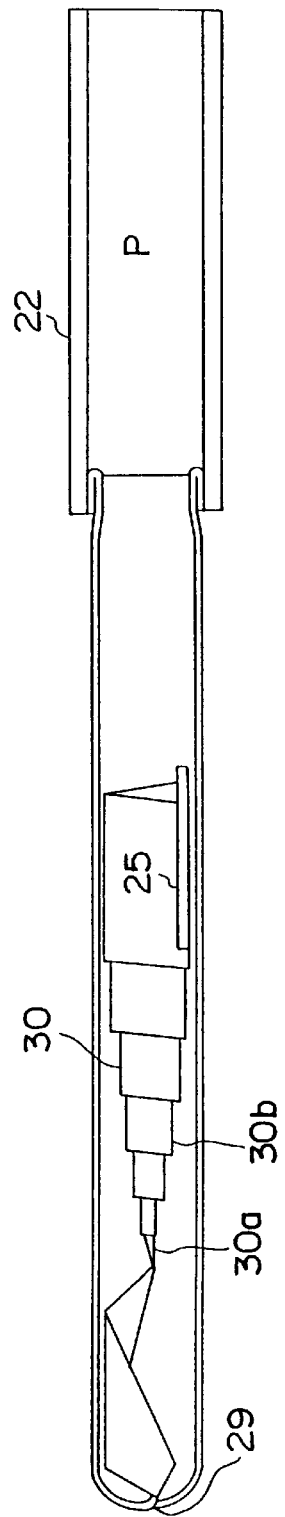

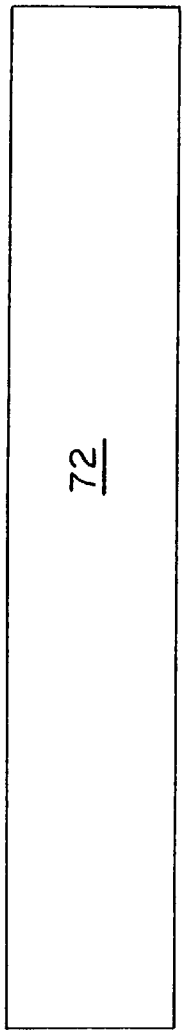
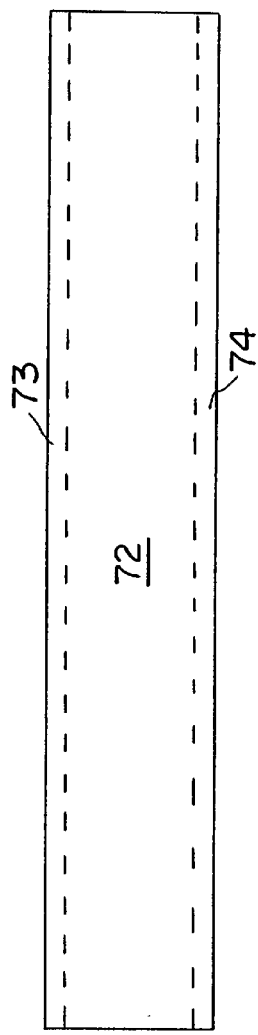
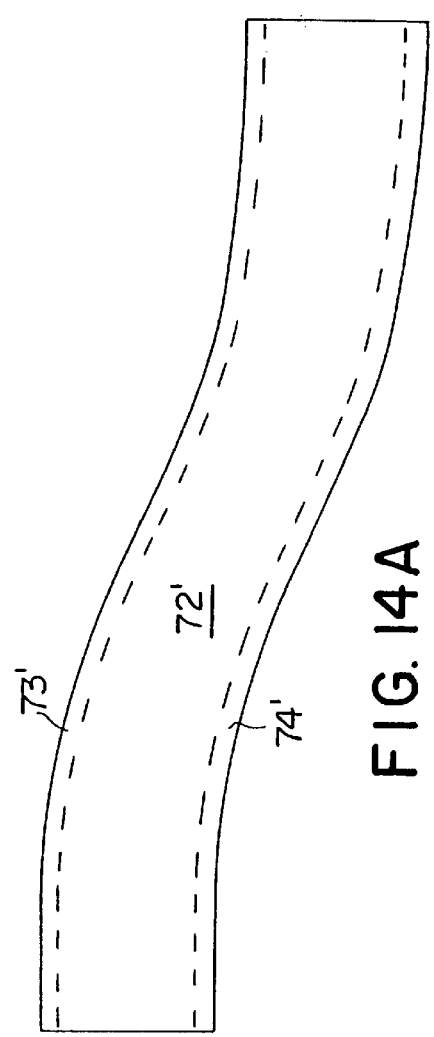
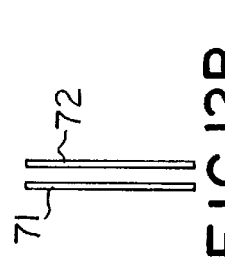
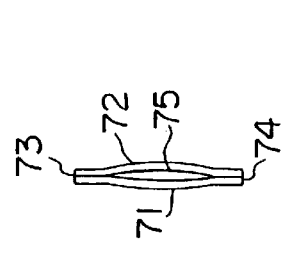
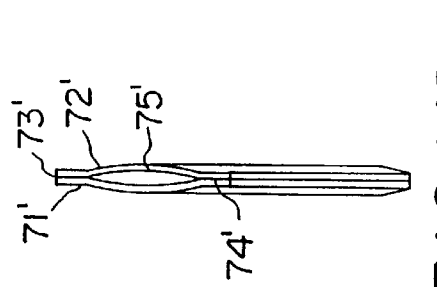

EVERTING TUBE STRUCTURE

CROSS-REFERENCE TO RELATED APPLICATIONS

This application claims priority benefit under 35 USC §119(e) of provisional application Ser. No. 60/032,295, filed Dec. 3, 1996.

BACKGROUND OF THE INVENTION

1. Field of the Invention

The present invention relates to an everting tube. More particularly, the present invention relates to a simple method of producing an everting tube from a flexible, collapsible tube and the structure so produced.

2. Description of the Prior Art

U.S. Pat. No. 3,050,060 (Hoffman) discloses a speculum liner and insemination rod combination. In particular, there is provided a speculum comprising a pasteboard, plastic or equivalent tube which is open-ended and about six inches long. However, this speculum tube is improved in that it is equipped with a practical anticontaminating means; more specifically, a simple paper or an equivalent liner. This liner was found to best take the form of a paper bag or envelope with the major portion and the closed end thereof protectively sheathed in the bore or passage of the speculum tube. The open end of the bag is bent or folded over the desired end (either end) of the speculum tube, wrapped tightly and attached permanently. Consequently, when the insemination rod is inserted and passed through the bore of the tube the leading end presses upon the closed imperforate end of the liner and it will gradually evert until the closed end projects a few inches beyond the leading end of the speculum tube and, when the envelope is tautened, the rod is forced through and beyond the closed end to do its intended job.

U.S. Pat. No. 3,168,092 (Silverman) discloses a medical probing instrument having flexible, extrudable tubing adapted to be extraverted under pressure into a body cavity. In particular, there is provided a closed housing or container having at one end a tubular projection of a diameter smaller than the cavity diameter, and generally of the approximate diameter of the thin-walled flexible tube to be placed inside of the cavity. A length of thin-walled flexible tubing with one end closed is placed inside the container (closed end first) through the tubular projection. The open end of the tubing is placed over the tubular projection of the container and clamped in pressure tight relation thereto. A means for introducing a gas or liquid under pressure inside the container is provided. The fluid pressure forces the tubing to be ejected out of the container through the tubular opening—being turned inside out as it goes. The internal fluid pressure enables the tubing to exert a pressure on the walls of the cavity to separate them and permit the tubing to be extruded and "grow" in length. The tubing can be retrieved by being physically withdrawn from the cavity, but preferably, it can be withdrawn by providing a cord or other tension member attached to the closed end inside the container, and to withdraw or wind up the cord by appropriate means, retrieving the tubing, all the while maintaining fluid pressure inside the tubing, by a procedure which is the direct reverse of the insertion process.

U.S. Pat. No. 3,433,214 (Silverman) discloses a method and apparatus for everting a tubular probe into a body cavity. The device consists of a tubular casing, a flexible, thin-walled tubular probe inside of the casing with the inside end closed and the outside end sealed circumferentially over a first end of the casing. The second end of the casing is closed. A reservoir of liquid is provided that can be raised above and lowered below the level of the casing. The reservoir is connected by a conduit to the casing. When the reservoir is raised, relative to the casing, liquid flows into the casing, causing the tubing to evert out of the end of the casing. When the reservoir is lowered, relative to the casing, liquid flows out of the casing, causing the tubing to be inverted back into the casing.

U.S. Pat. No. 3,502,069 (Silverman) discloses a method and apparatus for placing a tubular probe in a body cavity and for retrieving the probe from the body cavity. The instrument comprises a rigid tubular casing and a flexible eversible tubing inside the casing. One end of the tubing is closed and the other end is sealed circumferentially over an open end of the casing. The other end of the casing is closed. Means are provided to pump fluid into the casing, at a pressure higher than the pressure outside the casing, to evert the tubing out of the open end of the casing. Means are provided to pump fluid out of the casing, at a pressure lower than the pressure outside of the casing, to invert the tubing back into the casing.

U.S. Pat. No. 3,506,011 (Silverman) discloses a medical instrument for everting a thin walled flexible tubing. In particular, there is provided a length of collapsed thin walled tubing which is to be everted. A first end of the tubing is turned back on itself to form a cuff, providing an annular volume between the cuff and the collapsed tubing. A means to seal the cuff to the tubing is provided to close off the annular volume, and means are provided to insert fluid under pressure into the closed-off volume. The pressure causes the volume to expand longitudinally, drawing the collapsed tubing through the seal and causing it to be everted. The cuff is sealed to the tubing by being pressed into sliding sealing contact, or means such as a sealing ring is placed in the annulus. A disc with a central opening can be used with the tubing inserted through the opening turned back on itself and sealed circumferentially to the disc.

U.S. Pat. No. 3,589,356 (Silverman) discloses a method for everting and extraverting flexible tubing into a body cavity. In particular, one end of a tubing is closed and the other is sealed to a fluid pressure casing. The closed end of the tubing is initially disposed within the casing and a tension member passing through the casing is fixed to the reentrant tubing end. Instrumentation, radiation sources, etc. are transported by the tension member as the closed end everts through the tubing within the cavity. The everted tubing is retained within the cavity for a finite time and the initially closed end of the everted tubing may be opened.

U.S. Pat. No. 3,908,635 (Viek) discloses a simplified catheter structure including a disc adapted to be positioned in contact with the urethra meatus. The disc is provided with an aperture and a flexible tube is secured to the disc at the aperture. The flexible tube is adapted to be pushed through the aperture whereby the tube becomes everted in the urethra.

U.S. Pat. No. 3,911,927 (Rich, et al.) discloses an instrument for everting a flexible tubing into a body passage. In particular, the instrument comprises a rigid hollow casing having a flexible tubing located therein in such a manner that the hollow casing may be pressurized, the tubing everted out of the hollow casing and into the body passage. However, the tube is only partially everted into the body passage and then sealed so as to create a double-wall structure containing a pressurizing fluid between the walls. Thereafter, the hollow casing may be detached leaving the partially everted flexible tubing in the body passage.

U.S. Pat. No. 4,043,345 (Kramann, et al.) discloses a catheter. In particular, the catheter comprises a flexible hose attached to one end of a rigid tube through which fluid pressure may be applied to invert the hose from an invaginated position within said tube to an exserted position extending outwardly of said tube. At the distal end of the hose, a valve is provided which remains closed when the hose assumes its exserted position. The valve is formed at the distal end of the hose by cutting the distal end along a plane extending obliquely of the axis of the hose and forming the distal end walls of the hose in an abutting configuration defining therebetween an orifice which tends to remain closed by abutment of the distal end walls against each other when the hose is in its invaginated position, and particularly when fluid pressure is applied within the tube, with the abutting wall portions between which said orifice is defined tending to separate to open the orifice when the hose is exserted from the tube.

U.S. Pat. No. 4,077,610 (Masuda) discloses a method and apparatus for passing an article through the interior of a pipe. In particular, a turned-over or inverted section is formed at one end of a flexible, fluid impervious tube by turning the tube inside out and folding it back up on itself. With the turned-over end inserted in a pipe or conduit, the folded over end is secured to the pipe and then a fluid pressure differential is created between the inside of the tube in the pipe and the inside of the pipe ahead of the tube which differential is great enough to cause the turned-over end of the tube to migrate along the pipe from one end to the other by drawing the tube into the pipe from the end which is not attached to the pipe.

U.S. Pat. No. 4,109,659 (Sheridan) discloses urinary evagination catheters comprising a rigid tube and a flexible invaginated hose, provided with a stopper arrangement in the ported distal end of the hose that remains closed until the hose is fully everted from the tube at which point it automatically opens to permit fluid flow through the catheter. The catheter is produced by the steps of providing a substantially rigid tube open at both ends and a flexible hose shorter in length and smaller in diameter than said tube, said hose having a closed end, and an open end, the hose preferably tapering from the open end down to a smaller closed end. The hose advantageously has a varying wall thickness, being thicker at the large end of the taper and gradually thinning toward the small end. A port is cut in the side of the hose adjacent the closed end and leaving the tip as a pendant upon the now ported end of the hose. This tip is next inverted and inserted in the hose through the port forming a removable stopper for the hose port. The hose is then inserted small end first into the tube to such an extent that a short section of the open end of the hose remains outside of one end. This short section is folded back over the outside of the tube and a fluid-tight connection is made between the short section of hose and the adjoining outside of the tube, advantageously, by applying sealing material to the junction between the end of the hose and the outside of the tube.

U.S. Pat. No. 4,329,995 (Anthracite) discloses a catheter for nasotracheal aspiration of uncontaminated sputum specimens. In particular, the catheter is designed to be passed through the nasopharynx and into the trachea without contamination of the catheter lumen for obtaining uncontaminated sputum specimens. The catheter lumen is sealed to prevent entry of contaminants by the provision of a length of flexible, expandable tubing placed over and attached to the distal end of the catheter. The flexible tubing is rolled-up over a portion of its length and inverted into the unrolled portion, with the unrolled portion forming a cuff encircling the rolled-up portion to hold the rolled portion. A syringe pump connected to the opposite end of the catheter introduces fluid under pressure into the lumen of the catheter to expand the cuff and urge the rolled-up portion of the tubing from the cuff, and to unroll the tubing, whereby the lumen of the catheter is unsealed.

U.S. Pat. No. 4,493,711 (Chin, et al.) discloses a tubular extrusion catheter comprising an inverted-evertable non-elastic tube having a diameter throughout equal to or greater than the catheter body, an axially aligned end opening at the distal end, and a multifold configuration of the distal end to maintain end-sealing during inversion and eversion.

U.S. Pat. No. 4,530,698 (Goldstein, et al.) discloses a method and apparatus for traversing blood vessels. In particular, the everting tube principle is applied to an intravascular catheter system by utilizing the tube as a secondary catheter which everts from the leading end of a primary catheter tube. Thus, in use, the primary catheter tube of generally conventional form with the everting tube carried completely inside of it, is inserted into and worked through a blood vessel in the conventional manner and when the leading end of the primary tube has reached the limit of its travel, due either to further inaccessibility or length of travel, the everting tube, having its forward end attached to the leading end of the primary tube is everted from the leading end of the primary tube for further advancement along the blood vessel.

U.S. Pat. No. 4,604,094 (Shook) discloses a toposcopic catheter and method of fabrication. In particular, the everting catheter assembly includes a primary catheter tube inside of which an everting or toposcopic element is secured spaced from the distal end of the primary catheter tube and with the open head end of the toposcopic element facing away from the open distal end of the primary catheter. The bonding of the toposcopic element to the interior of the primary catheter is effected with the use of a hollow mandrel through which the toposcopic element extends so that a short length of the toposcopic element projects out from the mandrel and is folded back over a length of the outer surface of the mandrel at the mandrel forward end. The mandrel is withdrawn into the primary catheter tube to the desired location for bonding at which point a bond is effected by means of heat conducted to the mating surfaces through the catheter wall or deposited locally by a radiative technique and heating between the mating surfaces. The tail end of the everting catheter is secured into a seal tube of greater rigidity by disposing the open tail end of the toposcopic element over a bias-cut end of the seal tube. Bonding is effected by application of heat to the mating surfaces. The bias-cut on the seal tube permits complete collapse of the toposcopic element upon pressurization of the annular cylindrical region from which the eversion is effected. Since the protruding bias-cut does not preferentially bend so as to evert within itself, a geometrically unbalanced collapse of the toposcopic element occurs. Introduction of pressurized sterile eversion fluid media into the annular region is facilitated by means of a bleed tube extending to the lead end of the annular region so as to permit pre-existing gas to be bled from the annular region during pressurization.

U.S. Pat. No. 4,606,347 (Fogarty, et al.) discloses an inverted balloon catheter having sealed through lumen. In particular, the object of the disclosed invention is to provide a balloon catheter of the evertable-invertable type with a means for passing an object, such as a guide wire or a cannula, through the balloon while maintaining a sealed balloon system. This is accomplished, in a preferred way, by providing the free end of the balloon with a small axial elastomeric plug and providing the plug with a normally closed passageway, such as one formed by pushing a needle through the plug and by then withdrawing the needle. When the balloon is subject to inflation pressure, the plug acts as an imperforate part of the balloon whether or not a guide wire or the like is extending through the plug.

U.S. Pat. No. 5,045,070 (Grodecki, et al.) discloses a body cavity probe with an everting tube.

As may be ascertained, there are a number of medical instruments available for the probing and inspection of internal body cavities, such as the nose and throat passages, and many tubular conduits, e.g., the urinary tract; the sampling of contents from such cavities and the placement of medical treating devices therein. Many such instruments are of the rigid mechanical type that require either spreading of the walls of the cavity or the lubrication into such cavities of tubular metallic devices through which, after they are in place, additional instruments can be inserted. The insertion of these instruments may cause pressure and friction along the walls of the cavity, causing pain and discomfort, as well as injury to the tissues.

In an effort to overcome these problems, as shown by the above-noted documents, it has been proposed to line body cavities by means of a lining member which may be exserted or caused to protrude by the application thereto of a pressure medium in order to enable introduction of instruments into a body cavity lined in this fashion.

Nonetheless, a need continues for the provision of an everting tube structure of simple construction, which allows easy and/or self-administration, and which has an enhanced self-guiding ability.

SUMMARY OF THE INVENTION

A principal object of the everting tube structure of the present invention is the provision of a means for placement of a soft tube through a body passageway, such as the urinary tract, the nasal passages, the esophagus, the trachea or the intestines. The tube may be used for catheterization for various purposes. It may be used for the injection of therapeutic or diagnostic agents into body passageways or cavities. It may be used as a guide for the passage of another instrument, such as a visual apparatus, a biopsy tool, or a dilation catheter. It may be passed into a normal vein or artery, an occluded vein or artery, or it may be used to recanalize a complete thrombus prior to the injection into the occlusion zone of a fibrinolytic agent. It may be used for body cavity or passageway drainage purposes and also to provide an in-dwelling venous line for physiological measurements and delivery of drugs. Examples of such uses include the injection of drugs (e.g., Heparin, Lidocain, etc.) in patients with interstitial cystitis, drug delivery of antibiotics directly into the bladder, drug (e.g., BCG) for cancer patients, pre-procedural self-injected anaesthesia by patients, catheter insertion under pressure for patients with neurogenic bladders, as a replacement for Foley catheters, for dilation of the fallopian tubes, in lieu of naso-gastric tubes and others.

These objects and others, as will become apparent hereinafter, may be attained by the provision of an everting tube structure comprising: a flexible, collapsible tube having a first open end and a second open end, the flexible, collapsible tube having a first portion proximate the first open end and a second portion, the first portion having a first part adjacent the first open end and a second part adjacent the second portion, the second portion having been folded at an angle to the first portion and wound around the second part of the first portion to form a first hollow cylinder; and, a tube member having an open end, the first open end of the tube fluid-tightly, circumferentially attached to the open end of the tube member.

In another aspect of the invention, a method of making such an everting tube structure is provided. The method of making the everting tube structure comprises: providing a length of flexible, collapsible tube having a first open end and a second open end, the length of flexible, collapsible tube having a first portion proximate the first open end and a second portion, the first portion having a first part adjacent the first open end and a second part adjacent the second portion; folding the second portion at an angle to the first portion; winding the second portion around the second part of the first portion to form a first hollow cylinder; providing a tube member having an open end; fluid-tightly circumferentially attaching the first open end of the length of flexible, collapsible tube to the open end of the tube member.

BRIEF DESCRIPTION OF THE DRAWING FIGURES

FIGS. 2A–2D illustrate the everting tube structure of the present invention and its principle of operation.

FIGS. 3A and 3B illustrate a flexible, collapsible tube utilizable in the present invention, FIG. 3A being an end view of such a tube and FIG. 3B being a plan view of such a tube.

FIGS. 4A–4C illustrate the winding of the flexible, collapsible tube utilizable in the present invention, FIG. 4A being a plan view of a partially rolled tube, FIG. 4B being an end view thereof and FIG. 4C being an opposite end view thereof.

FIGS. 5A–5C illustrate the wound flexible, collapsible tube utilizable in the present invention, FIG. 5A is a plan view of a fully rolled tube, FIG. 5B being an end view thereof and FIG. 5C being an opposite end view thereof.

FIGS. 6A–6C illustrate another everting tube structure of the present invention and its principle of operation.

Figure 1:
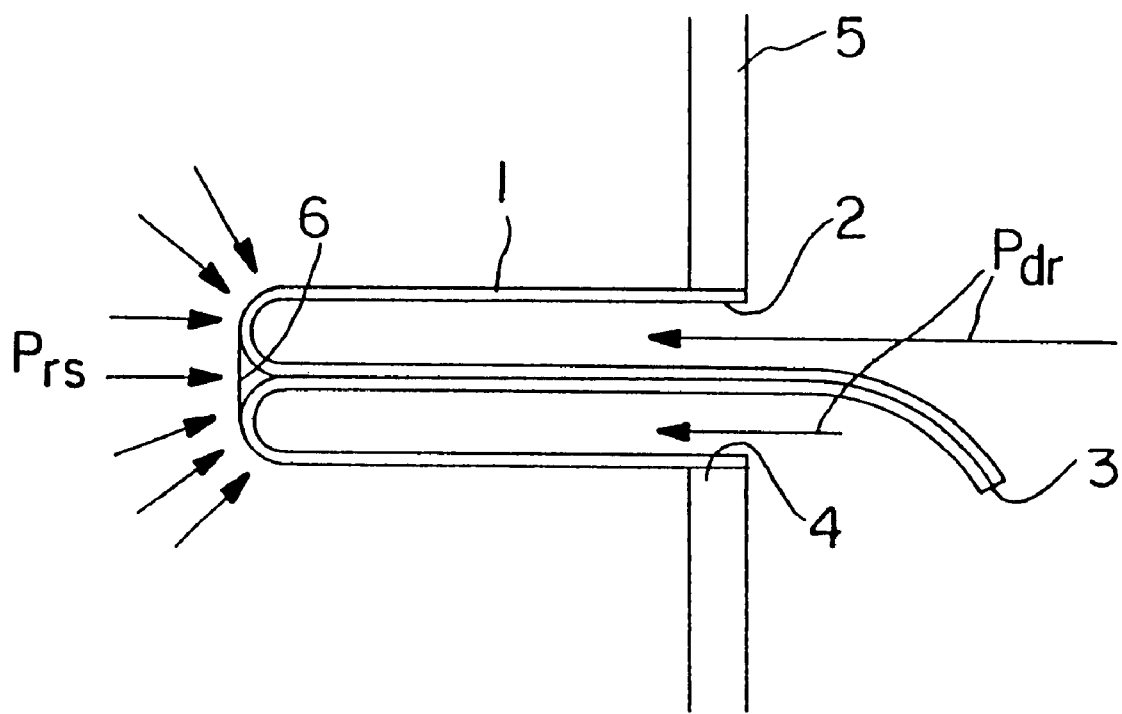
FIG. 1 illustrates the everting tube structure of a prior art device.

FIGS. 11A–11D schematically illustrate a method of forming the flexible, collapsible tube of the present invention.

FIGS. 12A, 12B, 13A and 13B schematically illustrate a preferred method of forming the flexible, collapsible tube of the present invention.

FIGS. 14A and 14B schematically illustrate an alternate shape or pattern for the flexible, collapsible tube of the present invention.

DETAILED DESCRIPTION OF THE INVENTION

In the method of passing foreign objects through body passages and/or into body cavities, a thrust force is utilized.

Depending on the shape, size, texture and reactive properties of the device and the passageway/cavity, the passage may prove difficult. If a guide tube is inserted prior to the device, it can facilitate the passing of that object. By passing a guide tube using the everting process, the guide tube can be easily inserted.

The need to pass devices into the body is an essential function done by doctors for the benefit of the patient. Depending on the flexibility or rigidity of the device, it may be difficult to guide them to the desired location. The path may be a tortuous one, it could cause natural reflexes in the patient, and may have other resistances. Forcing a device through can cause the patient discomfort and pain. It could also damage tissue that it contacts.

A thin walled tube passed before the insertion of the device would benefit both doctor and patient. The tube would act as a protective barrier between the patient's tissue and the device. Properly lubricated, the tube will guide the device if the path deviates from a linear route and could prevent the punching effect when the device veers off course. Most of the friction will be created between the thin walled tube and the device being passed. The exterior of the tube and the contacted tissue will slip slightly. If the tube is coated with appropriate medication, it could prevent possible complications later.

The everting process works by turning the tube inside out while advancing into the patient. As the tube everts, it dilates the path and lays a fresh surface onto the exposed tissue. There is little frictional force as it deploys. The path it follows will be the path of least resistance, so when a bend occurs, the everting tube will follow it.

The problem with the everting method is that for it to work, it must have one sealed end. The driving force of the everting tube is pressure. If a fluid is used as the pressure medium, the fluid pressure must be increased over the resistant force at the nose of the tube combined with the friction of the tube as it moves over itself. If the end of the tube is not sealed, the fluid will leak from the inside of the tube out through the everting end. If the leakage is large enough, the tube will not evert. With a small leak, it would move, but poorly and with little control. Of course, a seal would eliminate the propulsion problem but when the sheath is fully everted, the tube is not open and the passage of a medical device, etc. would be blocked by the seal.

The present invention provides an everting tube structure which maintains a seal until the tube is fully everted and then the seal opens leaving an open conduit for passage of medical devices, etc.

FIG. 1 illustrates a typical prior art structure wherein an everting tube 1 has an open end 2 and a closed end 3. The open end 2 is attached to an aperture 4 formed in a support 5. The application of driving pressure $P_{dr}$ to the open end 2 of the tube 1 causes the tube to evert, when the driving pressure $P_{dr}$ exceeds the resistive pressure $P_{rs}$ generated by dilation of the body passageway/cavity and frictional forces. When fully everted, however, a closed envelope has been inserted and it is then necessary to pierce the envelope in order to pass any medical device or the like through the tube. Moreover, the everting tube forms a rather blunt forward surface 6 which tends to impede forward progress of the tube.

FIG. 2A illustrates an everting tube structure of the present invention comprising a hollow cylinder 21 and a tube member 22.

The hollow cylinder 21 is formed from a length of flexible, collapsible tube 23, typically of circular cross-section (as best seen in FIG. 3A). The tube has a first open end 24 and a second open end 25. The tube has a first portion 26 proximate to the first open end 24 and a second portion 27. The first portion 26 has a first part 26a adjacent the first open end 24 and a second part 26b adjacent the second portion 27. The second portion 27 has been folded at an angle to the first portion 26 and wound around the second part 26b of the first portion (as best seen in FIGS. 4A, 4C, 5A and 5C to form a hollow cylinder 21 having an inner diameter "d" and an outer diameter "D".

The hollow cylinder 21 may be disposed within the tube member 22 and the first open end 24 of the tube may be fluid-tightly, circumferentially attached to an open end 28 of the tube member, as shown in FIG. 2A.

Figure 7A:
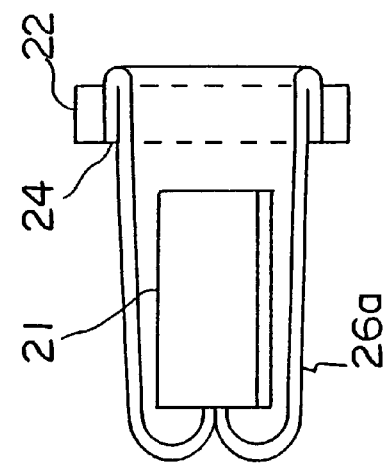
FIGS. 7A and 7B illustrate a further everting tube structure of the present invention.
Figure 7B:
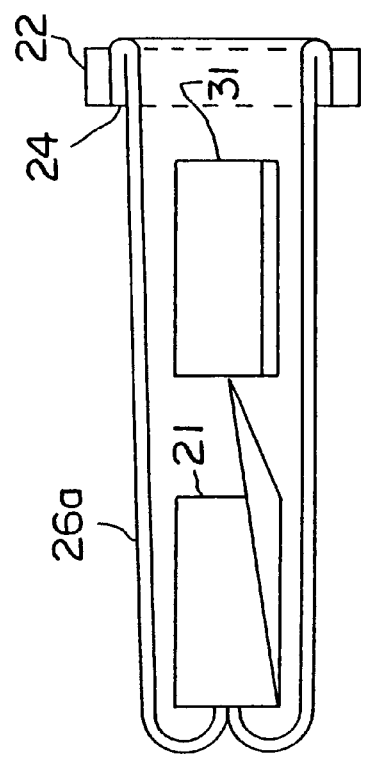

In another embodiment, as shown in FIGS. 7A and 7B, the first open end 24 of the tube may be fluid-tightly, circumferentially attached to an open end of a tube member 22, as shown in FIG. 7A, and then the first part 26a of the first portion of the flexible collapsible tube has been everted over the first hollow cylinder 21 to contain the same.

Figure 9A:
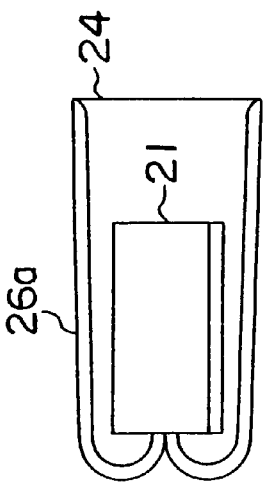
FIGS. 9A and 9B illustrate another everting tube structure of the present invention.
Figure 9B:
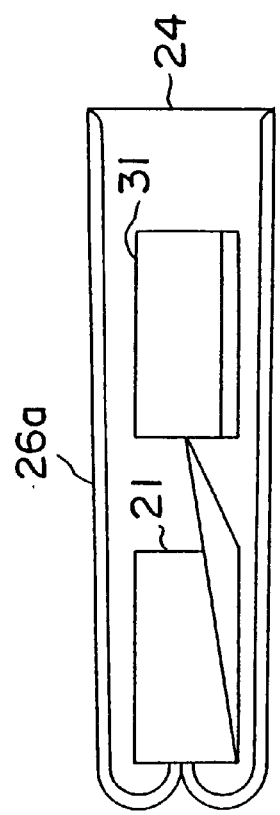

In yet another embodiment, as shown in FIGS. 9A and 9B, the first part 26a of the first portion of the flexible collapsible tube has been everted over the first hollow cylinder 21 to contain the same. The open end 24 can then be connected to various fittings, regardless of size.

As shown in FIG. 4A, while the second portion 27 is usually folded at right angles to the first portion 26, the second portion may be folded at an acute angle to the first portion, or at an obtuse angle to the second portion, as shown by phantom lines "a" and "b", respectively.

In operation, as best seen in FIGS. 2B–2C, the introduction of a fluid pressure medium P into the interior of pressure-resistant tube member 22 through aperture 28' causes the hollow cylinder 21 to begin to unroll and telescope out of itself, as best seen in FIG. 2B. Additional pressure medium P continues the unrolling and telescoping process, as best seen in FIG. 2C. However, in both instances, and until the tube is fully unrolled, the twist 29 maintains a fluid tight seal. When the tube is fully unrolled a complete and unimpeded passageway is provided by the open tube 23.

The key to everting a tube is to provide a large enough pressure "P" on the uneverted side of the tube without any pressure medium loss due to leakage. The best way to prevent leakage is to seal the end of the tube.

In essence, the present invention creates this seal using a simple technique, i.e., an "hour glass twist 29" is created at the everting end of the tube. The twist prevents any pressure medium from escaping from the interior of the sheath. Since no pressure medium is escaping from the everting end, the pressure within all parts of the interior of the everting tube is equal. With equal pressure, there is no seepage into the interior of the rolled tube section. Moreover, the hour glass twist is maintained for the whole everting process. This is achieved by the fact that the winding of the tube creates a spiral packing. As the tube everts, it is pulling new tube material forward, but, the interior tube approaches in a spiral pattern. This promotes and maintains the hour glass twist at the nose of the everting tube.

In those instances in which the length of the tube 23 would produce an outer diameter D of the hollow cylinder 21 in excess of the interior diameter of the pressure-resistant tube member 22, the tube may be wound in such a manner as to form multiple serially disposed hollow cylinders. In particular, a third portion 30, intermediate the second portion 27 and the second open end 25, has a first part 30a adjacent the second portion and a remainder part 30b adjacent the first part 30a. The remainder part 30b is folded at an angle to the first part 30a and wound about the first part 30a to form a second hollow cylinder 31. This further hollow cylinder may be serially disposed within the tube member 22, as best seen in FIG. 6A.

Figure 8A:
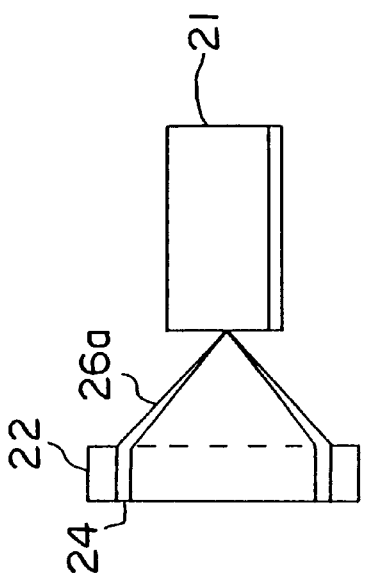
FIGS. 8A and 8B illustrate a further everting tube structure of the present invention utilizing multiple serial rolled sections.
Figure 8B:
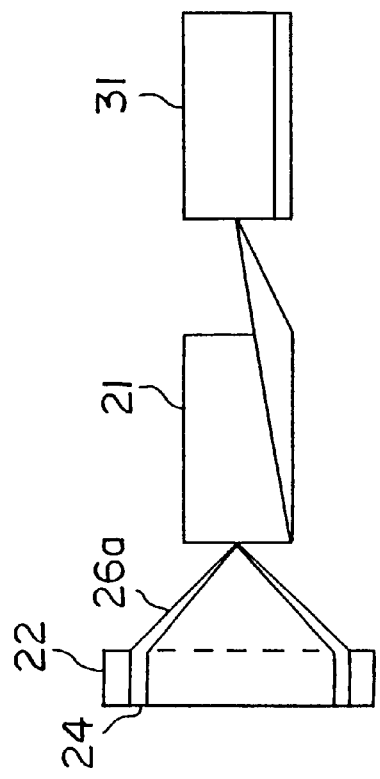

In another embodiment, as shown in FIGS. 8A and 8B, the first open 24 of the tube may be fluid-tightly, circumferentially attached to an open end of a tube member 22, as shown in FIG. 8A, and then the first part 26a of the first portion of the flexible collapsible tube has been everted over the hollow cylinders 21, 31 to contain the same.

Figure 10A:
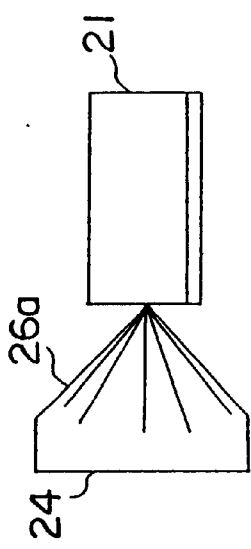
FIGS. 10A and 10B illustrate another everting tube structure of the present invention utilizing multiple serial rolled sections.
Figure 10B:
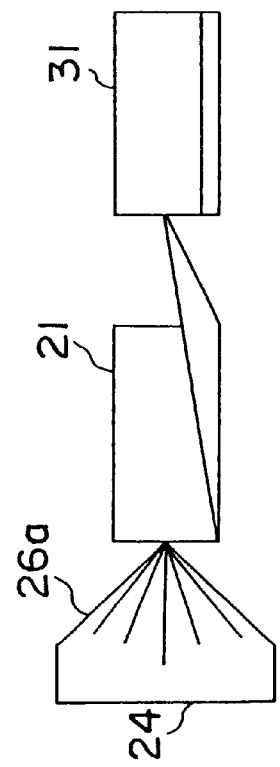
Figure 11A:
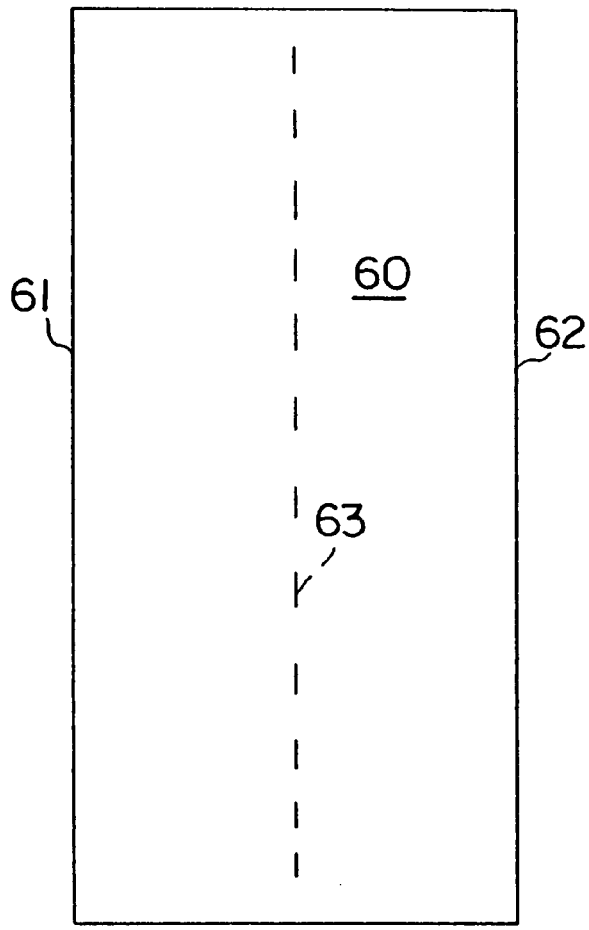
Figure 11B:
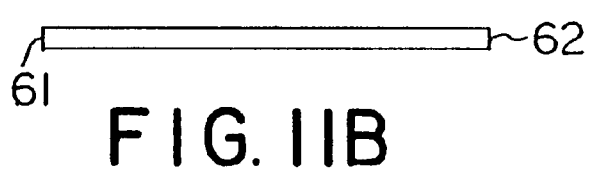
Figure 11C:
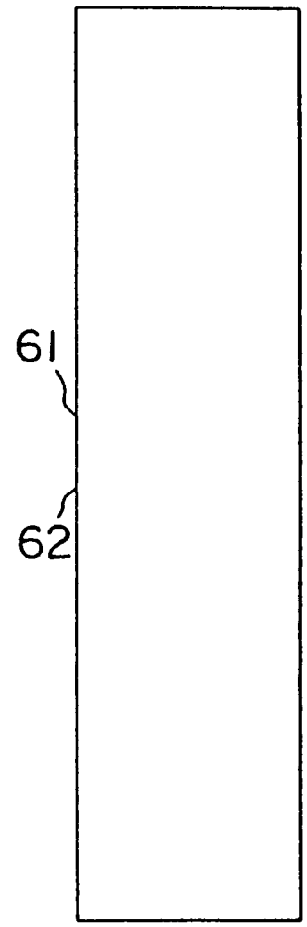
Figure 11D:
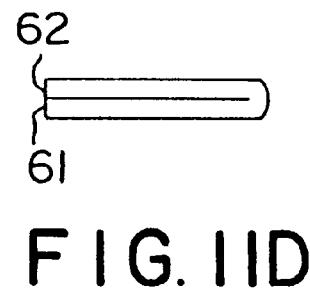

In yet another embodiment, as shown in FIGS. 10A and 10B, the first part 26a of the first portion of the flexible, collapsible tube has been everted over the hollow cylinders 21, 31 to contain the same. The open end 24 can then be connected to various fittings, regardless of size.

In a manner similar to that with one hollow cylinder, the introduction of a fluid pressure medium P into the interior of pressure-resistant tube member 22 causes the hollow cylinder 21 to begin to unroll and telescope out of itself, as best seen in FIG. 6B. Additional pressure medium P continues the unrolling and telescoping process, which begins to involve the second hollow cylinder 31, as best seen in FIG. 6C. The twist 29 is maintained until both hollow cylinders are fully unrolled.

Suitable materials from which the tube 23 may be formed include natural and synthetic rubber, silicone-based rubbers, polyurethane, polyolefins, copolymers of ethylene and vinyl acetate, polyvinyl chloride or copolymers of vinyl chloride and the like, preferably, polyurethane. The materials may include reinforcing materials such as synthetic fibers or threads derived from cotton, silk, nylon, polyester, etc.

Suitable materials from which the tube member 22 may be formed include metal, glass, polyolefins, polycarbonates, polymethylmethacrylate, nylon, polyesters, polystyrene, ethylene/vinyl acetate copolymers and the like. Non-rigid materials may also be utilized to form the tube member 22, so long as they have a sufficiently high resistance to deformation when pressurized as to cause the tube 23 to evert rather than the tube member significantly expand. For example, polyvinyl compounds such as Tygon® may be utilized.

The tube 23 may be fluid tightly attached to the tube member 22 by any conventional means or method, e.g., by adhesives, by melt sealing or by application of physical pressure, e.g., using an elastic cuff, etc. Preferably, a solvent bonding system based on tetrahydrofuran (THF) may be used. RF heating, i.e., melt bonding, can also be utilized.

While the tube 23 may be formed directly by extrusion, it has been found that a greater choice of materials of construction, especially with respect to thickness, may be obtained if the tube is manufactured from film.

As shown in FIGS. 11A–11D, a film 60 has a first longitudinal edge 61 and a second longitudinal edge 62. The film 60 is folded along a longitudinal fold line 63 to bring the first longitudinal edge 61 into contact with the second longitudinal edge 62. The longitudinal edges 61, 62 are then bonded to one another to produce the flexible, collapsible tube.

While the aforementioned "folding" technique can produce an operable system, it has been found that it is best to produce a tube which may lie as flat as possible.

In this regard, as shown in FIGS. 12A, 12B, 13A and 13B, two films, 71 and 72, are cut identically and superposed over one another. The edge portions, 73 and 74, are then bonded together to form a lumen 75, as best seen in FIGS. 13A and 13B.

As shown in FIGS. 14A and 14B, where elements similar to those of FIGS. 12A, 12B, 13A and 13B are similarly numbered, the pattern of the film need not follow a straight line, nor is a uniform cross-sectional perimeter needed. As long as the form can be rolled into a hollow cylinder, it can be utilized.

The bonding of the one film 71 to the other film 72 may be effected by an adhesive, by thermal sealing, chemical sealing, radio frequency heating or any other conventional technique for bonding such films together, so long as it does not adversely affect the everting properties of the tube.

In fact, any conventional bonding system and joint form can be utilized so long as it does not adversely affect the everting properties of the tube.

What is claimed is:

1. An everting tube structure comprising:
   a flexible collapsible tube having a first open end and a second open end, said flexible collapsible tube having a first portion proximate said first open end and a second portion, said first portion having a first part adjacent said first open end and a second part adjacent said second portion, said second portion having been folded at an angle to said first portion and wound around said second part of said first portion to form a first hollow cylinder; and
   a tube member having an open end, said first open end of said tube fluid-tightly, circumferentially attached to said open end of said tube member.

2. The everting tube structure according to claim 1, wherein said first hollow cylinder is disposed within said tube member.

3. The everting tube structure according to claim 1, wherein said first part of said first portion of said flexible collapsible tube has been everted over said first hollow cylinder to contain the same.

4. The everting tube structure according to claim 1, wherein said flexible collapsible tube further comprises a third portion, said third portion being intermediate said second portion and said second open end, said third portion having a first part adjacent said second portion and a remainder part adjacent said first part, of said third portions said remainder part having been folded at an angle to said first part of said third portion and wound around said first part of said third portion to form a second hollow cylinder, said second hollow cylinder being serially disposed with respect to said second hollow cylinder.

5. The everting tube structure according to claim 4, wherein said first hollow cylinder and said second hollow cylinder are disposed within said tube member.

6. The everting tube structure according to claim 4, wherein said first part of said first portion of said flexible collapsible tube has been everted over said first hollow cylinder and said second hollow cylinder to serially contain the same.

7. The everting tube structure according to claim 1, wherein said second portion has been folded at an acute angle to said first portion.

8. The everting tube structure according to claim 1, wherein said second portion has been folded at an obtuse angle to said first portion.

9. The everting tube structure according to claim 1, wherein said second portion has been folded at a right angle to said first portion.

10. The everting tube structure according to claim 1, wherein said tube member includes an aperture for introducing a pressurizing fluid thereinto whereby said flexible collapsible tube may be everted.

11. A method for making an everting tube structure, comprising:

provision a length of flexible, collapsible tube having a first open end and a second open end, said length of flexible, collapsible tube having a first portion proximate said first open end and a second portion, said first portion having a first part adjacent said first open end and a second part adjacent said second portion folding said second portion at an angle to said first portion;

winding said second portion around said second part of said first portion to form a first hollow cylinder;

providing a tube member having an open end;

fluid-tightly, circumferentially attaching said first open end of said length of flexible, collapsible tube to said open end of said tube member.

12. The method according to claim 11, wherein said length of flexible, collapsible tube having a first open end and a second open end is formed by providing a first film having a first longitudinal edge portion and a second longitudinal edge portion;

providing a second film having a first longitudinal edge portion and a second longitudinal edge portion;

superposing said second film over said first film with said first edge portion of said second film superposed over said first edge portion of said first film and said second edge portion of said second film superposed over said second edge portion of said first film;

fluid tightly bonding said first edge portions to each other and fluid-tightly bonding said second edge portions to each other to form said length of tube.

13. The method according to claim 11, wherein said first hollow cylinder is inserted within said tube member.

14. The method according to claim 11, wherein said first part of said first portion of said flexible collapsible tube is everted over said first hollow cylinder to contain the same.

* * * * *